US006475786B1

(12) United States Patent
Bordignon et al.

(10) Patent No.: US 6,475,786 B1
(45) Date of Patent: Nov. 5, 2002

(54) AMPHOTROPIC RETROVIRUS PACKAGING CELL LINE, PROCESS FOR ITS PRODUCTION AND USE THEREOF

(75) Inventors: Claudio Bordignon, Milan (IT); Bernhard Goller, Penzberg (DE); Ruediger Rueger, Huglfing (DE); Georg Tiefenthaler, Sindelsdorf (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/700,979

(22) PCT Filed: May 14, 1999

(86) PCT No.: PCT/EP99/03304

§ 371 (c)(1),
(2), (4) Date: Jun. 11, 2001

(87) PCT Pub. No.: WO99/60143

PCT Pub. Date: Nov. 25, 1999

(30) Foreign Application Priority Data

May 20, 1998 (EP) .............................................. 98109135

(51) Int. Cl.$^7$ ................................................ C12N 5/00
(52) U.S. Cl. .................................... 435/325; 435/235.1
(58) Field of Search ............................. 536/23.1, 23.4, 536/24.1, 24.2; 435/320.1, 325, 235.1; 530/350, 420

(56) References Cited

U.S. PATENT DOCUMENTS 5,591,624 A * 11/1993 Barber et al. ............ 435/240.2

5,716,832 A   8/1998 Barber et al.

FOREIGN PATENT DOCUMENTS

WO   WO 8907150   8/1989

OTHER PUBLICATIONS

Chattopadhyay et al, *J. Virol.*, 39, pp. 777–791 (1981).
Cone and Mulligan, *Proc. Natl. Acad.Sci. USA*, 81, pp. 6349–6353.
Mann et al, *Cell*, 33, pp. 153–156 (1983).
Markowitz et al, *J. Virol.*, 62, pp. 1120–1124 (1988).
Markowitz et al, *Virology*, 167, pp. 400–406 (1988).
Martinez et al, *Virology*, 208, pp. 234–241 (1995).
Miller et al., *Mol. Cell Biol.*, 6, pp. 2895–2902 (1986).
Miller et al, *Mol. Cell Biol.*, 5, pp. 431–437 (1985).
Soneoka Y et al, *Nucleic Acids Research*, 23, No. 4, pp. 628–633 (1995).
Markowitz D et al, *Annals of The New York Academy of Sciences*, 612, pp. 407–414 (1990).

\* cited by examiner

*Primary Examiner*—Sean McGarry
*Assistant Examiner*—Janet Epps
(74) *Attorney, Agent, or Firm*—George W. Johnston; John P. Parise

(57) ABSTRACT

A titer of retroviral vectors of at least about $10^7$ colony-forming units/ml cell culture supernatants is obtained using an amphotropic retroviral packaging cell line which contains functional gag, pol and env genes integrated into the genome in which the expression of the genes gag and pol is regulated independently of the expression of the env genes, wherein the genome of the said cell line contains one or two functionally active env genes.

4 Claims, No Drawings

AMPHOTROPIC RETROVIRUS PACKAGING CELL LINE, PROCESS FOR ITS PRODUCTION AND USE THEREOF

The invention concerns an improved amphotropic retroviral packaging cell line, a process for its production as well as its use especially for gene therapy in vitro and in vivo. High virus titres can be achieved with retroviral vectors which are produced by such a packaging cell line.

Retroviral vectors are widely used to transfer foreign genes into cells of mammals and humans. However, for safety reasons such retroviral vectors should no longer be replication-competent. For this reason packaging cell lines are used to produce retroviral vectors which are not able to produce wild-type virus since they contain no functional packaging sequences. Such packaging cell lines have been known and described for a long time: Ψ2 (Mann et al., Cell 33 (1983) 153–156), Ψ-Am (Cone and Mulligan, Proc. Natl. Acad. Sci. USA 81 (1994) 6349–6353), PA12 (Miller et al., Mol. Cell Biol. 5 (1985) 431–437), GP+E-86 (Markowitz et al., J. Virol. 62 (1988) 1120–1124), PA317 (Miller and Buttimore, Mol. Cell Biol.6 (1986) 2895–2902), and GP+env Am12 (Markowitz et al., Virology 167 (1988) 400–406), see also "Handbuch der molekularen Medizin", Vol. 1 Ed. D. Ganten and K. Ruckpaul, Springer Publishers, Heidelberg 1997, R. Rüger, chapter 2.1, 197–241.

However, all these packaging cell lines except for GP+env Am12 (referred to as Am12 in the following) lead to a certain extent to the formation of wild-type virus (Bosselman et al., Mol.Cell Biol. 7 (1987) 1797–1804). In contrast Am12 in which the viral gag and pol functions are introduced into the cell on one plasmid and env is introduced into the cell on another plasmid, is a safe packaging cell line. These functions are therefore integrated in different loci of the packaging cell genome. In order to form Nvld-type virus from Am12 three recombinations have to occur which restore the original intact genome. This appears to be almost impossible and also has previously not been observed.

In order to avoid the problems caused by homologous recombination in packaging cell lines attempts have for example also been made to express gag/pol and env by different promoters (Meyers et al., Arch.Virol. 119 (1991) 257–264; Dougherty et al., J.Virol. 63 (1989) 3209–3212) and to use packaging cell lines based on spleen necrosis virus (SNV) (Mlartinez and Dornburg, Virology 208 (1995) 234–241).

However, a disadvantage of the known packaging cell lines is that the vector-virus titres of the retroviral vectors produced in this manner are very low and range between $10^2$ and a maximum of $10^6$ colony-forming units (CFU)/ml cell culture supernatant.

The object of the invention is to provide retroviral, safe packaging cell lines which are able to produce vector viruses with a high transduction efficiency.

The invention concerns an amphotropic retroviral packaging cell line which contains functional gag, pol and env genes integrated into the genome in which the expression of the genes gag and pol is regulated independently of the expression of the env genes characterized in that the genome of the said cell line contains one or two functionally active env genes.

A further subject matter of the invention is a process for producing a retroviral vector characterized in that an amphotropic retroviral packaging cell line according to the invention is transfected with a vector-virus (vector genome) which contains one or more genes that are heterologous for the virus but contains no functionally active retroviral structural genes in which the cell line is cultured and the retroviral vector is isolated from the culture supernatant.

A further subject matter of the invention is a process for producing an amphotropic retroviral packaging cell line characterized in that an env helper plasmid containing a selection gene and a gag/pol helper plasmid containing a selection gene are transfected into a eukaryotic cell, transfected cells are identified on the basis of the selection gene and are isolated and those cells are selected which contain one or two functionally-active env genes.

A further subject matter of the invention is a replication-incompetent retroviral vector virus which has been produced by the method according to the invention.

It has turned out that the number of env integrates in the genome of a packaging cell line has a decisive influence on the transduction efficiency of the vector-viruses produced in this manner. This is all the more surprising since it is known from Martinez and Dornburg, Virology 208 (1995) 234–241 that the extent of env expression in a packaging cell line would not have an influence on the transduction efficiency. The packaging cell lines examined by Martinez and Dornburg differ with respect to env expression only in the promoter strength of the sequences regulating env expression.

In a preferred embodiment the packaging cell line according to the invention contains two env integrates and a gag/pol integrate. According to the invention use of the packaging cell line achieves a titre of retroviral vectors of 2 $10^6$ to $10^7$ or more, preferably at least $10^7$ colony-forming units/ml cell culture supernatant and/or preferably a transduction efficiency of at least 50% in MOLT-4 cells (ATCC CRL 1582) after three days measured by the centrifugation method.

The independent regulation of the gene expression of gag/pol and env is usually achieved by locating at least one expression control sequence and/or a stop signal between gag/pol and env.

Starting cell lines for the packaging cell line are for example 3T3, D17. Suitable starting vectors are based on, for example, MLV, MoMuLV. Such suitable packaging cell lines and starting vectors are known to a person skilled in the art and are described for example by R. Rüger (1997) in "Handbuch der molekularen Medizin".

The cell line HSR BM01 is particularly preferred as a packaging cell line according to the invention. This cell line was deposited on Dec. 9, 1995 by Boehringer Mannheim GmbH according to the Budapest Contract in the "Deutsche Sammlung von Mikroorganismen und Zellkulturen GmbH" (DSM), Mascheroder Weg 1b, 38124 Braunschweig under the No. DSM ACC 2235.

A further subject matter of the invention is a process for producing an amphotropic retroviral packaging cell line according to the invention.

An amphotropic split genome retroviral packaging cell line can for example be produced as described in Markowitz et al., Virology 167 (1988) 400–406. Two plasmids are used for this which code for the so-called f helper sequences (gag, pol and env).

In order to select cell lines according to the invention, the number of env and gag/pol integrates has to be determined. This is expediently carried out by digesting the genomic DNA with restriction enzymes which do not cleave in the gag/pol sequences or env sequences and determining the number of fragments which contain gag/pol- or env-specific sequences.

The invention whose protective scope results from the patent claims is further elucidated by the following examples and publications. The described methods are to be understood as examples which still describe the subject matter of the invention even after modifications.

EXAMPLE 1
Construction of Helper Plasmid
Construction of the gag/pol Helper Plasmid A helper plasmid carries the viral structural genes gag/pol of the Moloney murine leukaemia virus (MoMULV) e.g. under the control of the MoMULV 5'LTR. These structural genes gag/pol together with the 5'LTR can be obtained from the proviral DNA of MoMULV by restriction digestion. In this process it is important for safety reasons to inactivate the so-called packaging sequences Ψ. This can for example be achieved by a deletion which is introduced with the aid of a restriction digestion. Furthermore it is advantageous to have a selectable marker such as e.g. the gpt gene on the helper plasmid the gene product of which imparts resistance to the selection drug mycophenolic acid. Mycophenolic acid resistance allows the rapid selection of clones which have taken up the desired plasmid (gag/pol helper plasmid). A corresponding helper plasmid can be constructed as described for example by Markowitz et al., J. Virol. 62 (1988) 1120–1124.

Construction of the env Helper Plasmid

Another helper plasmid carries the viral structural gene env of the amphotropic murine leukaemia virus clone 4070A (4070A) (Chattopadhyay et al., J. Virol. 39 (1981) 777–791) e.g. under the control of MoMULV 5'LTR. For this a fragment of the proviral DNA of 4070A which contains the env gene and the 3' acceptor splice site is isolated. This fragment is cloned into a plasmid which contains the MoMULV 5'LTR as well as the 5' donor splice site. A corresponding helper plasmid can be produced as described for example by Markowitz et al., Virology 167 (1988) 400–406.

EXAMPLE 2
Transfer of the Helper Constructs
Transfer of the gag/pol Helper Plasmid NIH 3T3 cells (ATCC No. CRL 1658) are for example firstly transfected with the gag/pol helper plasmid. This can for example be carried out with the aid of electroporation. Transfected cells can be isolated with the aid of a suitable selection medium since the gpt gene is present on the gag/pol plasmid. A suitable selection medium contains for example hypoxanthine (15 µg/ml), xanthine (250 µg/ml) and mycophenolic acid (25 µg/ml) (HXM medium). Resistant clones can be subsequently examined for the expression of reverse transcriptase (RT) as for example described by Markowitz et al., J.Virol. 62 (1988) 1120–1124. A clone that expresses to a particularly high degree is selected for subsequent transfection with the env helper plasmid.

Transfer of the env Helper Plasmid

Subsequently the env helper plasmid can be transfected for example with the aid of electroporation into a gag/pol-transfected, mycophenolic acid-resistant clone with high RT activity. In order to simply identify successfully transfected cells it is advantageous to for example co-transfect a further plasmid which contains a resistant gene together with the helper plasmid. This can for example be a plasmid which imparts resistance to hygromycin such as for example the plasmid pRSHhyg (Murphy, A. J. (1987) doctoral thesis, Columbia University, USA). Successfully transfected clones can be simply selected with the aid of a suitable selection medium which for example contains 200 µg/ml hygromycin B. Hygromycin-resistant clones can be subsequently examined for env expression with the aid of radioimmunoprecipitation using an env antiserum as for example described in Markowitz et al., Virology 167 (1988) 400–406.

EXAMPLE 3
Selection of Amphotropic Retroviral Packaging Cell Lines

The number of copies of the env helper plasmid integrated into the genome was selected as a parameter for choosing a certain subclone of a packaging cell line. Martinez and Dornburg, Virology 208 (1995) 234–241 have showed that, in contrast to gag/pol, a higher env expression has no influence on the virus titre; the titre of clones with a higher gag/pol but not a higher env expression correlated with the found infection efficiency. This was the basis for the assumption that the ratio of gag/pol to env gene products may be very important for the efficiency of packaging cells and possibly packaging cells with a lower env expression may lead to viral supernatants with a higher transduction efficiency.

Determination of the Number of env Integrates

The number of copies of the env helper plasmid integrated into the genome of the individually examined clones was determined with the aid of restriction digestion and Southern blot analysis. For this genomic DNA was isolated from various subclones and digested with the aid of restriction enzymes e.g. the enzyme PstI. This enzyme does not cleave in the env sequence and only cleaves once in the entire plasmid sequence. Since each corresponding second cleavage site which leads to the respective restriction fragment is located randomly in the genome, it is possible in this manner to determine the number of env integrates.

The digested DNA was separated in an Agarose gel and transferred onto a nylon membrane by means of capillary transfer. The fragments which contain env-specific sequences were detected with the aid of an env-specific, digoxigenin-labelled DNA probe. Subclones with different numbers of env integrates were found. For example the band sizes that were obtained after digestion with the restriction enzyme PstI were 17.5 kb, 13.3 kb and 3.4 kb for the packaging cell line GP+env Am12 and 13.3 kb and 3.4 kb for the packaging cell line HSR BM01.

EXAMPLE 4
Production of Virus-producing Cell Lines with Different Numbers of env Integrates Each subclone was transfected either with two (HSR BM01) or three (GP+env Am12) env integrates containing the retroviral construct pL1 in order to produce virus-producing cell lines (producer lines). The construct pL1 carries the cDNA for a shortened form of the human low affinity nerve growth factor receptor (hΔLNGFR (produced analogously to WO 95/06723)) in which the cytoplasmic domain is deleted and which is under the control of the viral 5'=0 LTR. The gene product of the hΔLNGFR cDNA, a membrane protein, can be detected on the cells with the aid of a hΔLNGFR-specific monoclonal antibody (mAb). Virus-producing clones were isolated from HSR BM01 (HSRBM-L1) as well as from GP+env Am12 (clone C11-C4) with the aid of immunofluorescence and flow cytometry.

Determination of the Titre of Supernatants from Virus-Producing Cells Containing Different Numbers of env Integrates Indicator cells (NIH/3T3; ATCC No. CRL 1658) were transduced with the supernatants containing virus particles from the two clones HSRBM-L1 or C11-C4. A cytochemical staining method based on the anti-hΔLNGFR mAb allows the determination of the number of colony-forming units (titre) of hΔLNGFR-coding retroviruses. Whereas the supernatant of the producer line C11-C4 (3 env copies) based on the packaging cell GP+env Am12 had a titre of $6.3 \times 10^5$ colony-forming units, the supernatant of the producer line HSRBM-L1 (two env copies) based on HSR BM01 had a titre of $1.25 \times 10^7$.

EXAMPLE 5
Transduction of Various Cell Lines with Supernatants from Two Different Producer Cell Lines which Contain the Same Retroviral Vector The cell lines Jurkat, MOLT4, Raji and K 562 are cultured in RPMI/10% FCS under normal cell culture conditions and transduced at cell densities of $3-9\times10^5$ cells/ml. The various producer cell lines which contain an identical retroviral vector are cultured in DMEM/10% FCS under normal cell culture conditions. The cells are seeded at $1\times10^4$ cells/cm$^2$. After three days the supernatant is discarded and fresh medium is added. The supernatant is harvested 24 hours later. The supernatant is filtered through a 0.22 μm filter. The titre of the various supernatants is determined and adjusted such that equivalent volume amounts contain an equivalent number of virus particles. The titre of the retroviral supernatant was determined using the method of immune staining titration using NIH3T3 as target cells.

Transduction
Protocol 1

$5\times10^5$ cells are resuspended in 1 ml retroviral supernatant. The transduction is carried out in a 24-well plate. After centrifugation (1000 g, 30° C., 90 min.) the cells are washed and resuspended in 1 ml fresh cell culture medium. The cells are incubated overnight and 1 ml fresh medium is added. Three days after transduction the cells are harvested and stained with an FITC-labelled anti-LNGFR antibody. The percentage of LNGFR-expressing cells is determined by means of flow cytometry. In this process dead cells are excluded from the analysis by propidium iodide staining. The flow-cytometry analysis is carried out on a FACScan instrument.

Protocol 2

The procedure in protocol 2 was carried out according to protocol 1, but without centrifugation. The cells are incubated for two hours at 37° C. with the retroviral supernatant.

Table 1 shows the LNGFR expression of various cell lines three days after transduction according to protocol 1.

Table 2 shows the LNGFR expression of various cell lines three days after transduction according to protocol 2.

TABLE 1

| | % LNGFR-positive cells three days after transduction (centrifugation method) | |
|---|---|---|
| | HSR BM01 (HSRBM-L1) | GP + envAm12 (clone C11–C4) |
| K562 | 88.81 | 12.79 |
| MOLT4 | 53.64 | 3.52 |
| RAJI | 25.31 | 8.83 |
| JURKAT | 44.36 | 3.96 |

TABLE 2

| | % LNGFR-positive cells three days after transduction (incubation method) | |
|---|---|---|
| | HSR BM01 (HSRBM-L1) | GP + envAm12 (clone C11–C4) |
| K562 | 68.69 | 8.24 |
| MOLT4 | 37.86 | 2.68 |

TABLE 2-continued

| | % LNGFR-positive cells three days after transduction (incubation method) | |
|---|---|---|
| | HSR BM01 (HSRBM-L1) | GP + envAm12 (clone C11–C4) |
| RAJI | 6.72 | 3.01 |
| JURKAT | 23.91 | 4.64 |

LIST OF REFERENCES

Bosselman et al., Mol. Cell Biol. 7 (1987) 1797–1804
Chattopadhyay et al., J. Virol. 39 (1981) 777–791
Cone and Mulligan, Proc. Natl. Acad. Sci. USA 81 (1994) 6349–6353
Dougherty et al., J. Virol. 63 (1989) 3209–3212
Handbuch der molekularen Medizin, Volume I, Ed. D. Ganten and K. Ruckpaul, Springer Verlag Heidelberg 1997, R. Rüger, Chapter 2.1, 197–241
Mann et al., Cell 33 (1983) 153–156
Markowitz et al., J. Virol. 62 (1988) 1120–1124
Markowitz et al., Virology 167 (1988) 400–406
Martinez and Dornburg, Virology 208 (1995) 234–241
Meyers et al., Arch. Virol. 119 (1991) 257–264
Miller and Buttimore, Mol. Cell Biol. 6 (1986) 2895–2902
Miller et al., Mol. Cell Biol. 5 (1985) 431–437
Murphy, A. J. (1987), Doctoral Thesis, Columbia University, USA

What is claimed is:

1. An amphotropic retroviral packaging cell line, each packaging cell containing exactly one functional gag gene, exactly one functional pol gene and exactly two functional env genes, the genes being integrated into the genome in such a manner that the expression of the gag and pol genes is regulated independently of the expression of the env genes and a titre of at least $10^7$ colony-forming units/ml cell culture supernatant is achieved by the packaging cell line when packaging a retroviral vector.

2. A process for producing an amphotropic retroviral packaging cell line, which comprises transfecting a eukaryotic cell with an env helper plasmid containing a selection gene and a gag/pol helper plasmid containing a selection gene, identifying the transfected cells on the basis of the selection gene, and isolating those cells which contain two functionally active env genes.

3. The packaging cell line DSM ACC 2235.

4. A process for the production of a retroviral vector, which comprises (i) transfecting a eukaryotic cell with an env helper plasmid containing a selection gene and a gag/pol helper plasmid containing a selection, (ii) identifying the transfected cells on the basis of the selection gene, (iii) isolating those cells which contain two functionally active env genes, (iv) transfecting the isolated cells with a vector genome which contains one or more heterologous genes for the virus but contains no functionally active retroviral structural genes, (v) culturing the cells, and (vi) isolating the retroviral vector from the culture supernatant.

* * * * *